(12) United States Patent
Yoshida et al.

(10) Patent No.: US 11,378,577 B2
(45) Date of Patent: Jul. 5, 2022

(54) REAGENT AND METHOD FOR MEASURING THROMBIN-ANTITHROMBIN COMPLEX

(71) Applicant: LSI MEDIENCE CORPORATION, Tokyo (JP)

(72) Inventors: Tatsuya Yoshida, Tokyo (JP); Yuhang Yang, Tokyo (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 330 days.

(21) Appl. No.: 15/772,037

(22) PCT Filed: Oct. 31, 2016

(86) PCT No.: PCT/JP2016/082364
§ 371 (c)(1),
(2) Date: Apr. 27, 2018

(87) PCT Pub. No.: WO2017/073795
PCT Pub. Date: May 4, 2017

(65) Prior Publication Data
US 2018/0238871 A1 Aug. 23, 2018

(30) Foreign Application Priority Data
Oct. 30, 2015 (JP) ............................. JP2015-215162

(51) Int. Cl.
*G01N 33/52* (2006.01)
*G01N 33/543* (2006.01)
*G01N 33/545* (2006.01)

(52) U.S. Cl.
CPC ..... *G01N 33/54393* (2013.01); *G01N 33/543* (2013.01); *G01N 33/545* (2013.01); *G01N 33/54306* (2013.01); *G01N 2333/8128* (2013.01); *G01N 2333/974* (2013.01)

(58) Field of Classification Search
CPC .......... G01N 33/54393; G01N 33/543; G01N 33/54306; G01N 33/545; G01N 2333/8128; G01N 2333/974; G01N 33/536; G01N 33/86
See application file for complete search history.

(56) References Cited

U.S. PATENT DOCUMENTS

| 4,199,502 | A | 4/1980 | Babson |
| 5,705,396 | A | 1/1998 | Fickenscher |
| 2001/0007774 | A1 | 7/2001 | Saitoh et al. |
| 2015/0212075 | A1* | 7/2015 | Hattori ............. G01N 33/54313 436/501 |
| 2018/0106793 | A1 | 4/2018 | Yoshida et al. |

FOREIGN PATENT DOCUMENTS

| EP | 0 391 433 A2 | 10/1990 |
| EP | 0 669 344 A2 | 8/1995 |
| EP | 2 881 738 A1 | 6/2015 |
| JP | S62-138187 A | 6/1987 |
| JP | H07-238099 A | 9/1995 |
| JP | H08-068794 A | 3/1996 |
| JP | H10-026621 A | 1/1998 |
| JP | 2001-221800 A | 8/2001 |
| JP | 2001-289850 A | 10/2001 |
| JP | 2002-316999 A | 10/2002 |
| JP | 2011-038903 A | 2/2011 |

(Continued)

OTHER PUBLICATIONS

E. A. Padlan, Adv Prot Chem 49:57-133; 1996.*
Corada et al., Blood, 2001; 97:1679-84.*
National Blood Alliance (2008;retrieved from https://www.stoptheclot.org/news/treatment-of-thrombosis/.*
International Preliminary Report on Patentability in connection with International Patent Application No. PCT/JP2016/082364 dated May 11, 2018.
International Search Report in connection with PCT/JP2016/082364 dated Jan. 31, 2017.
Soe, G., and I. Kohno, The Specific Detection of the Thrombin-Antithrombin III Complex by Latex Agglutination "Kecchu thrombin-Antithrombin III Fukugotai no Sokuteiho", Bulletin of the Ogata Institute for Medical and Chemical Research 1990: p. 29-33, Aug. 1, 1991.

(Continued)

*Primary Examiner* — Carmencita M Belei
(74) *Attorney, Agent, or Firm* — Knobbe, Martens, Olson & Bear, LLP

(57) ABSTRACT

Provided is a reagent for assaying a thrombin-antithrombin complex (TAT) in a blood sample from a subject by latex agglutination assay. The reagent includes a polycation. As a result, TAT complexes can be precisely assayed while circumventing the effect of heparin. The polycation is, for example, hexadimethrine bromide, chitosans, modified dextran, aminodextran, hydroxymethyl cellulose trimethylamine, lysozyme, spermine, spermidine, polylysine, polyarginine, polyornithine, protamine sulfate, hydroxyethyl cellulose trimethylamine, heparin-binding protein, polyallylamine, polyallylamine hydrochloride, poly(diallyl dialkyl amine), polyamideamine, polyamine, polyvinylbenzyltrimethylammonium chloride, polydiallyldimethylammonium chloride, polyethyleneimine, polypropyleneimine, polypropylethyleneimine, polyimidazoline, polyvinylamine, polyvinyl pyridine, poly(acrylamide/methacryloxypropyltrimethylammonium bromide), poly(diaryldimethylammonium chloride/N-isopropylacrylamide), poly(dimethylaminoethyl acrylate/acrylamide), poly(dimethylaminoethyl methacrylate), polydimethylaminoepichlorohydrin, polyethyleneiminoepichlorohydrin, polymethacryloxyethyl-trimethylammonium bromide, hydroxypropylmethacryloyloxyethyl dimethyl ammonium chloride, poly(methyldiethylaminoethylmethacrylate/acrylamide), poly(methyl/guanidine), polymethylvinylpyridinium bromide, poly(vinylpyrrolidone-dimethylaminoethyl methacrylate), or polyvinylmethylpyridinium bromide.

3 Claims, 8 Drawing Sheets

(56) References Cited

FOREIGN PATENT DOCUMENTS

| JP | WO2014/021387 | * | 6/2014 | ........... G01N 33/543 |
| JP | 2016-194444 A | | 11/2016 | |
| JP | 2016-194445 A | | 11/2016 | |

OTHER PUBLICATIONS

Extended European Search Report received in connection with European Patent Application No. 16860023.7 dated Feb. 26, 2019.
Elgue, G., et al., The Use of a Commercial ELISA for Assay of Thrombin-Antithrombin Complexes in Purified Systems, Thrombosis and Haemostasis 63(3):435-438, Jun. 28, 1990.
Jorpes, E., et al., Neutralisation of Action of Heparin by Protamine, The Lancet 2:975-976, Nov. 4, 1939.
Okajima, Y., et al., Studies on the Neutralizing Mechanism of Antithrombin Activity of Heparin by Protamine, Thrombosis Research 24(1-2):21-29, Oct. 1, 1981.
Patel, J.P., Polybrene Can Neutralise Enoxaparin in Plasma Being Tested for Thrombin Generation, However This Effect Is Concentration Dependent, Journal of Thrombosis and Haemostasis 9(S2), Abstract P-MO-228, Jul. 31, 2011.
Sugiyama, T., et al., Study on Neutralization of Low Molecular Weight Heparin (LHG) by Protamine Sulfate and Its Neutralization Characteristics, Thrombosis Research 68(2):119-129, Oct. 15, 1992.
Soe, G., and I. Kono, The Specific Detection of the Thrombin-Antithrombin III Cornplex by Latex Agglutination "Kecchu thrombin-Antithrombin III Fukugotai no Sokuteiho", Bulletin of the Ogata Institute for Medical and Chemical Research 1990: p. 29-33, Aug. 1, 1991.

* cited by examiner

REAGENT AND METHOD FOR MEASURING THROMBIN-ANTITHROMBIN COMPLEX

TECHNICAL FIELD

The present invention relates to a reagent and a method for assaying the thrombin (T)-antithrombin (AT) complex (TAT) in a sample.

BACKGROUND ART

The thrombin-antithrombin complex (TAT) is a protein complex produced in blood in the course of blood coagulation, and the quantification of TAT complexes in blood is useful for the diagnosis of thrombosis, such as disseminated intravascular coagulation (DIC). However, the abundance of TAT complex is approximately $1/100,000$ of the abundance of free antithrombin, and, therefore, the measurement of TAT complex is not easy.

Examples of a currently prevailing TAT quantification method include methods using reagent kits employing enzyme immunoassay (ELISA) technologies, such as Enzygnost (registered trademark) TAT micro from Siemens AG, and reagent kits employing chemiluminescent enzyme immunoassay (CLEIA) technologies, such as STACIA (registered trademark) CLEIA TAT from LSI Medience Co. However, any of them are assay methods requiring separation between solid and liquid phases (B/F separation), which need laborious washing operations by hands or by special machines.

Patent Literature 1 to 4 have reported reagent systems based on latex agglutination assay in no need of B/F separation, any of which aims to assay samples prepared by diluting TAT complexes synthesized ex vivo with a buffer solution. However, there is no report on any reagent that enables the precise concentration of TAT complexes in human samples to be measured using latex agglutination assay. Moreover, in any of these literatures, the effect of the cross-reactivity of an antibody used is circumvented by establishing a TAT assay reagent based on the specificity thereof or by adding an additive agent. Patent Literature 5 discloses an assay of TAT by a sandwich assay method using an antibody with no cross-reactivity but the assay lacks sufficient sensitivity for clinical use.

Accordingly, there has been a need for a reagent and a method for assaying TAT complexes in a biological sample with high sensitivity and high accuracy based on latex agglutination assay, which is characterized by simplified measurement operations.

The present inventors reported reagents enabling the precise concentration of TAT complexes in human samples to be measured using latex agglutination assay in no need of B/F separation (Patent Literatures 6 and 7). However, the reagents have been susceptible to further improvement for clinical applications.

CITATION LIST

Patent Literature

Patent Literature 1: Japanese Patent Laid-open (Kokai) No. 2001-289850
Patent Literature 2: Japanese Patent Laid-open (Kokai) No. 2001-221800
Patent Literature 3: Japanese Patent Laid-open (Kokai) No. 07-238099
Patent Literature 4: Japanese Patent Laid-open (Kokai) No. 2002-316999
Patent Literature 5: Japanese Patent Laid-open (Kokai) No. 03-48158
Patent Literature 6: Japanese Patent Application No. 2015-074168
Patent Literature 7: Japanese Patent Application No. 2015-074173

SUMMARY OF INVENTION

Technical Problem

As illustrated in FIG. 1, two antibodies of an antibody which recognizes a TAT complex by binding to the antithrombin part of the TAT complex and an antibody which recognizes a TAT complex by binding to the thrombin part of the TAT complex are used in an assay of the TAT complex based on latex agglutination assay. In theory, only when the TAT complex exists, both antibodies bind to each other, latex agglutination occurs, and the TAT complex can be quantified.

However, examination by the present inventors revealed that even when a monoclonal antibody of which the reactivity to TAT is 100 or more times higher than the reactivity to antithrombin is used as an antibody binding to the antithrombin part of such a TAT complex as used in Patent Literatures 6 and 7, nonspecific reaction occurs due to the influence of heparin (particularly unfractionated heparin) used as an anticoagulant in treatment of thromboembolism or DIC, or the like, and inaccurate assay results are yielded. This may be considered because heparin forms, together with antithrombin, complexes in blood, thereby allowing antithrombin to be a multimer. Such a heparin-antithrombin complex is considered to have a structure more similar to the structure of antithrombin in the case of forming TAT complexes in comparison with typical antithrombin, and is considered to form more multimers. Thus, in the case of assaying a sample from a patient receiving heparin, even when latex particles coupled to a monoclonal antibody of which the reactivity to TAT complexes is 100 or more times higher than the reactivity to antithrombin are used, the particles recognize heparin-antithrombin complexes and singly agglutinate, and such agglutination as nonspecific reaction is added to this reaction. Such nonspecific reaction due to heparin-antithrombin complexes is a problem which does not occur in an assay method enabling B/F separation and which is peculiar to a TAT assay reagent employing latex agglutination assay, found for the first time by the present inventors.

Such methods as described in Patent Literature 1 and 2 are known as methods for circumventing the effect of antithrombin in a TAT assay reagent by conventional latex agglutination assay. However, it has not been suggested at all that antithrombin multimer is generated by heparin. A method for circumventing the effect of antithrombin allowed to be a multimer by heparin has not been suggested at all.

Thus, the present invention is to provide a reagent and a method for assaying TAT complexes in a biological sample using latex agglutination assay requiring neither B/F separation nor washing operations, wherein the effect of heparin and the like is circumvented, and TAT complexes can be precisely assayed.

Solution to Problem

As a result of intensive examination for solving such problems, the present inventor found that addition of a polycation such as hexadimethrine bromide into a TAT assay reagent enables circumvention of the nonspecific agglutination of heparin-antithrombin complexes and the precise assay of TAT complexes in a biological sample. The present invention was thus accomplished.

That is, the present invention will provide the following items.

[1] A reagent for assaying a thrombin-antithrombin complex (TAT) in a blood sample from a subject by latex agglutination assay, the reagent comprising a polycation.

[2] The reagent according to [1], wherein the subject is a patient receiving heparin.

[3] The reagent according to [1] or [2], wherein the polycation is selected from the group consisting of hexadimethrine bromide, chitosans, modified dextran, aminodextran, hydroxymethyl cellulose trimethylamine, lysozyme, spermine, spermidine, polylysine, polyarginine, polyomithine, protamine sulfate, hydroxyethyl cellulose trimethylamine, heparin-binding protein, polyallylamine, polyallylamine hydrochloride, poly(diallyl dialkyl amine), polyamideamine, polyamine, polyvinylbenzyltrimethylammonium chloride, polydiallyldimethylammonium chloride, polyethyleneimine, polypropyleneimine, polypropylethyleneimine, polyimidazoline, polyvinylamine, polyvinyl pyridine, poly(acrylamide/methacryloxypropyltrimethylammonium bromide), poly(diaryldimethylammonium chloride/N-isopropylacrylamide), poly(dimethylaminoethyl acrylate/acrylamide), poly(dimethylaminoethyl methacrylate), polydimethylaminoepichlorohydrin, polyethyleneiminoepichlorohydrin, polymethacryloxyethyl-trimethylammonium bromide, hydroxypropylmethacryloyloxyethyl dimethyl ammonium chloride, poly(methyldiethylaminoethylmethacrylate/acylamide), poly(methylguanidine), polymethylvinylpyridinium bromide, poly(vinylpyrrolidone-dimethylaminoethyl methacrylate), and polyvinylmethylpyridinium bromide.

[4] The reagent according to [1] or [2], wherein the polycation is selected from the group consisting of hexadimethrine bromide, polyalkylene amines such as polyethyleneimine and polypropylethyleneimine, protamine sulfate, polylysine, polyornithine, and aminodextran.

[5] The reagent according to any one of [1] to [4], wherein the reagent comprises a first anti-TAT antibody which recognizes a TAT complex by binding to an antithrombin part of the TAT complex bound to latex and a second anti-TAT antibody which recognizes a TAT complex by binding to a thrombin part of the TAT complex bound to latex.

[6] The reagent according to [5], wherein the first anti-TAT antibody is an antibody of which reactivity to a TAT complex is 100 or more times higher than reactivity to free antithrombin.

[7] A method for assaying a TAT complex existing in a blood sample from a subject, the method comprising assaying a TAT complex by performing latex agglutination assay using the reagent according to any one of [1] to [6].

[8] The method according to [7], wherein the subject is a patient receiving heparin.

Advantageous Effects of Invention

According to the present invention, a reagent based on latex agglutination assay enables a slight amount of TAT complexes in a biological sample to be precisely assayed (quantified) while circumventing the effect of heparin. As a result, precise TAT assay based on latex agglutination assay even with plasma from a patient receiving heparin (or plasma sampled through a heparin blood-collecting vessel) is enabled. It is diagnostically useful that TAT complexes in a sample from a patient receiving heparin also used for treatment of DIC can be precisely assayed.

DETAILED DESCRIPTION OF THE PREFERRED EMBODIMENT

Figure 1:
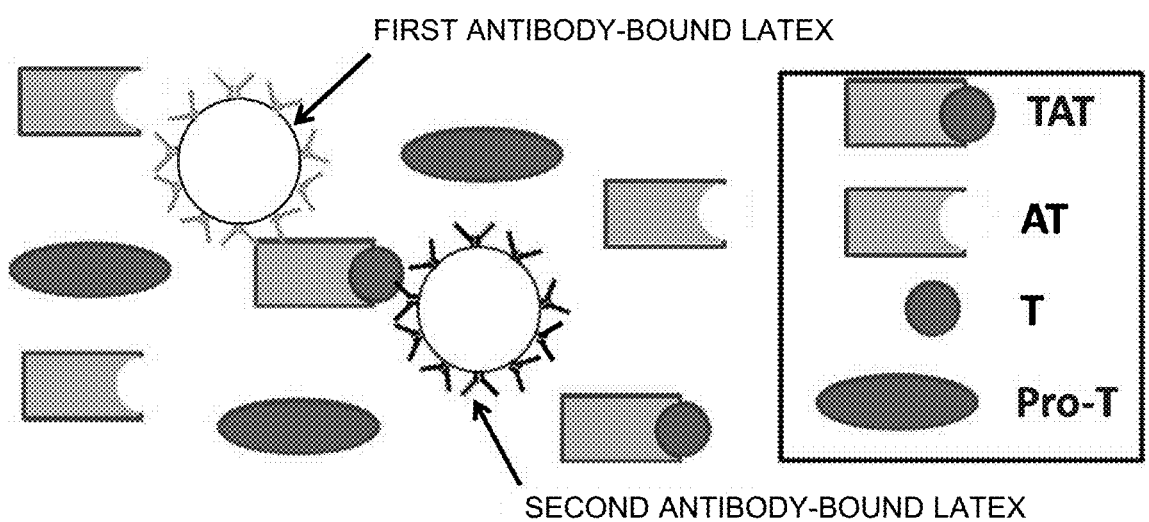
FIG. 1 is a schematic view of a TAT assay method based on latex agglutination assay.

A TAT assay reagent of the present invention is:
a reagent for assaying thrombin-antithrombin complexes (TAT) in a blood sample from a subject by latex agglutination assay. The reagent comprises a polycation.

An example of the TAT assay reagent of the present invention will be described as one embodiment below. However, the scope of the present invention is not limited thereto.

The TAT assay reagent of the present invention is preferably an immunoassay reagent for assaying TAT complexes in a biological sample by latex agglutination assay in a sandwich system using latex particles coupled to each of two anti-TAT antibodies.

For example, an antibody (first antibody) which recognizes a TAT complex by binding to the antithrombin part of the TAT complex and an antibody (second antibody) which recognizes a TAT complex by binding to the thrombin part of the TAT complex can be used in combination as antibodies which can be used in the present invention.

The first antibody may be an antibody which can recognize a TAT complex by binding to the antithrombin part of the TAT complex. An antibody of which the reactivity to the TAT complex is at least 100 or more times higher than the reactivity to free antithrombin is preferably used. The reactivity of the first antibody to the TAT complex may be 100 or more times higher than the reactivity to free antithrombin and is more preferably 200 or more times higher, still more preferably 1,000 or more times higher, and particularly preferably 10,000 or more times higher than the reactivity to free antithrombin. The maximum extent of cross-reactivity is not particularly specified because a lower level of cross-reactivity is better, but the cross-reactivity to free antithrombin may be, for example, 100,000 times or 50,000 times less than the reactivity to TAT.

In the preparation of the antibody, either free antithrombin or TAT may be used for the immunization in animals other than human and the resulting antibody may be used in the present invention as long as it can recognize a TAT complex by binding to the antithrombin part of the TAT complex.

As used in the present invention, the phrase "binding to the antithrombin part" means binding to antithrombin in a complex (TAT) formed by the association of free antithrombin, which is most abundant in a sample, with free thrombin. Accordingly, in cases where the antithrombin in a conformation achieved when it forms the complex is referred to as antithrombin in the complex-form structure and the antithrombin in a conformation achieved when it does not form the complex is referred to as antithrombin in the free-form structure (free antithrombin), the phrase "binding to the antithrombin part" means binding to the antithrombin in the complex-form structure.

The antithrombin in the free-form structure has a conformation different from that of the antithrombin in the complex-form structure. The reason is that the antithrombin in the free-form structure changes its conformation through the formation of a complex associated with free thrombin and maintains the changed conformation.

The ratio of TAT to free antithrombin which fails to form TAT both present in a living body is considered to range from 1:60,000 to 1:110,000 on the basis of the range measured in normal subjects and generally considered to be approximately 1:100,000. Moreover, although it is known that the ratio may be changed in patients with sepsis and/or hepatic diseases, the ratio is considered to be around 1:50,000 even in cases where the amount of free antithrombin is relatively low. Thus, if the first antibody also has reactivity to free antithrombin, the quantification of TAT will become difficult. Thus, an antibody having a low level of reactivity to free antithrombin should be used for the quantification of TAT. Therefore, an antibody having a level of reactivity to TAT that is 100 or more times higher than the reactivity to free antithrombin is used.

As used in the present invention, the phrase "a level of reactivity to TAT that is 100 or more times higher than the reactivity to free antithrombin" refers to a case where the ratio of the affinities for individual antigens is 100 or more, a case where the ratio of the amounts of antigens required to exhibit a certain inhibition rate in measurement by means of indirect inhibition ELISA described below is 100 or more, and the like.

An antibody having a level of reactivity to TAT that is 100 or more times higher than the reactivity to free antithrombin can be obtained by a method described in the Examples described later. The case where the antibody is examined or screened by indirect inhibition ELISA will be described below.

At first, an antibody which recognizes a TAT complex by binding to the antithrombin part of the TAT complex (a candidate antibody for the first antibody) is prepared. Such an antibody as an antibody directed against a binding site on the antithrombin part of the TAT complex and recognizing the complex may be selected from antibodies obtained in advance by a method, such as the method described below to prepare monoclonal antibodies by hybridoma cells. Of course, a previously known antibody directed against a binding site on the antithrombin part of the TAT complex and recognizing the complex would likewise be used in the assessment system below.

That is, a candidate antibody is allowed to react with a solution containing TAT or an antigen capable of inhibiting the reaction with TAT in a certain amount (for example, 0.1, 0.5, 1, 5, 10, 50 µg/mL) for a sufficient period of time (for example, 12 hours). Then, the reaction liquid is allowed to react with a TAT-immobilized substrate for a certain period of time. Subsequently, after washing, a labeled secondary antibody is used to measure the amount of the antibody bound to the TAT on the substrate (the percentage of residual antibody).

For example, at first, a certain amount of TAT complexes are immobilized onto a substrate, such as a plate, under a condition where any antigen that inhibits the reaction with the corresponding antibody is not present. Those skilled in the art will be able to appropriately determine the amount of the antigen (TAT) immobilized onto a substrate in view of the relationships between the quantity of the used antigen and the type of the assessed antibody.

The above-described candidate antibody for the first antibody in each concentration (for example, 0.04 to 1 µg/mL) is allowed to react with the above-described TAT-immobilized substrate for a certain period of time under a condition where any antigen that inhibits the reaction with the corresponding antibody is not present. Subsequently, after washing, a labeled secondary antibody (anti-mouse IgG-HRP) is used to measure the amount of the antibody bound to the TAT on the substrate. The concentration of the antibody which gives an absorbance of around 1.0 (corresponding to 1000 according to the method described in Table 1) is determined. This antibody concentration can be considered to be a concentration of the antibody in the inhibition with the antigen (Table 3; concentration during the reaction [µg/mL]).

Next, the candidate antibody in a concentration determined by the above-described method is allowed to react with a solution containing TAT or free antithrombin in a certain amount (for example, 0.1, 0.5, 1, 5, 10, 50 µg/mL) for a sufficient period of time (for example, 12 hours). Then, the reaction liquid is allowed to react with a TAT-immobilized substrate for a certain period of time. Subsequently, after washing, a labeled secondary antibody (anti-mouse IgG-HRP) is used to measure the amount of the antibody bound to the TAT on the substrate (the percentage of residual antibody).

Additionally, the percentage of residual antibody can be calculated relative to the detection value obtained for the case where absorption with antigen is not performed, which is considered as 100%.

In cases where the reactivity of the antibody to free antithrombin is high, the antibody capable of binding to TAT is decreased in amount and thus the antibody detected by the labeled secondary antibody is decreased in amount (the percentage of residual antibody is decreased), while in cases where the reactivity of the antibody to free antithrombin is low, a more amount of the antibody remains capable of binding to TAT and thus the antibody detected by the labeled secondary antibody is increased in amount (the percentage of residual antibody is increased).

This percentage of residual antibody will be compared with a percentage of residual antibody obtained when the antibody is first reacted with TAT (the inhibition reaction is performed with TAT) and then the reaction liquid is reacted with the immobilized TAT.

Next, in cases where, for example, a percentage of residual antibody of 50% is obtained in the inhibition reaction by adding free antithrombin to a concentration of 50 µg/mL, the amount of TAT required to achieve the same percentage of residual antibody is calculated based on the above-described result from the inhibition with TAT. In cases where the amount of the TAT inhibitory antigen required to achieve a percentage of residual antibody of 50% is less than 0.50 µg/mL when the inhibition is performed with TAT, the reactivity to TAT can be considered to be 100 or more times higher than the reactivity to free antithrombin.

The thus selected antibody can be selected as a first antibody. Additionally, in cases where the first antibody is a monoclonal antibody, its affinity (Kd) for TAT is preferably equal to or less than $10^{-8}$. However, those skilled in the art will be able to appropriately select an antibody suitable for a latex reagent based on the affinity value for TAT.

In cases where an antibody capable of recognizing a TAT complex by binding to the antithrombin part of the TAT complex is selected as the first antibody, the second antibody is not limited as long as it is an antibody which can recognize a TAT complex by binding to the thrombin part of the TAT complex, but an antibody which specifically reacts with thrombin can be used. Even an antibody which has cross-reactivity to free thrombin may often be used because free thrombin molecules are quite rare in a sample. Those skilled in the art will be able to select and use appropriate antibodies.

In the preparation of the above-described antibody, either free thrombin or TAT may be used for the immunization in animals other than human and the resulting antibody may be used in the present invention as long as it can recognize a TAT complex by binding to the thrombin part of the TAT complex.

As used in the present invention, the phrase "binding to the thrombin part" means binding to thrombin in a complex (TAT) formed by the association of free thrombin, which is present in a sample, with antithrombin. Accordingly, in cases where the thrombin in a conformation achieved when it forms the complex is referred to as thrombin in the complex-form structure and the thrombin in a conformation achieved when it does not form the complex is referred to as thrombin in the free-form structure, the phrase "binding to the thrombin part" means binding to the thrombin in the complex-form structure.

It is possible that the thrombin in the free-form structure has a conformation different from that of the thrombin in the complex-form structure. The reason is that the thrombin in the free-form structure changes its conformation through the formation of a complex associated with antithrombin and maintains the changed conformation.

The second antibody is not particularly limited as long as being an antibody which recognizes a TAT complex by binding to the thrombin part of the TAT complex. In the case of a monoclonal antibody, its affinity (Kd) for TAT is preferably equal to or less than $10^{-8}$. However, those skilled in the art will be able to appropriately select an antibody suitable for a latex reagent based on the affinity value for TAT.

For example, two antibodies which specifically bind to TAT complexes, i.e., which fail to react with thrombin and antithrombin but specifically react only with TAT complexes and have different epitopes can be used in combination as antibodies used in the present invention Either polyclonal or monoclonal antibodies may be used for the above-described first and second antibodies. Those skilled in the art will be able to obtain these antibodies according to known procedures.

Animals such as sheep, horse, goat, rabbit, mouse, rat, and the like may be used as animals to be immunized with an immunogen for the preparation of an antibody, and rabbit, goat, and the like are preferably used especially for the preparation of polyclonal antibodies. Moreover, monoclonal antibodies can be obtained by known methods to prepare hybridoma cells, and mouse, rat, rabbit or the like is preferably used in that case. Hybridoma cells and monoclonal antibodies can be prepared according to conventional methods, for example, methods described in "Zoku-Seikagaku Jikken Koza" (Biochemical Experiment Training Course; The Japanese Biochemical Society, ed.) or "Men-eki Seikagaku Kenkyu-hou" (Immuno-biochemical research methods; The Japanese Biochemical Society, ed.).

TAT may be used as an immunogen, as described above. Alternatively, an antibody produced by using a complex associated with vitronectin, VTAT, as an immunogen can also be used in the present invention. Moreover, antithrombin and thrombin may be used for the first and second antibodies, respectively.

For these immunogens, TAT complexes purified from a raw material, that is, a sample collected from a living body or TAT complexes synthesized in vitro by combining free thrombin and free antithrombin molecules may be used. The synthetic TAT complexes may be, for example, TAT complexes obtained by incubating in vitro thrombin and antithrombin molecules available as biologics, while TAT complexes expressed using a known translation system such as those in E. coli, mammalian cells, insect cells infected with baculovirus, and the like may be recovered, purified, and used as an immunogen.

Moreover, in cases where immunity to recognize a difference in conformation can be induced with a partial peptide alone, specifically, in cases where it is desired in the production of an antibody to specify the binding site of the antibody, partial peptides of antithrombin and thrombin may be used for the production of the first and second antibodies, respectively. In that case, as a method of selecting a peptide sequence for an antigen, a method of synthesizing a peptide fragment, and an immunization method, known methods can be used.

Examples of the antibody used in the present invention include antibody fragments. The antibody fragments are fragments of a desired antibody, which moreover have the same reactivity as that of the original antibody. Examples of an antibody fragment that can be used in the present invention include fragments such as Fab, Fab', F(ab')$_2$, or Fv. Any of these fragments can be obtained, for example, by digestion of an antibody with a protein degradation enzyme according to a conventional method, followed by separation and purification according to conventional methods for protein separation and purification. These fragments may be directly immobilized onto latex particles and used, while fragments may be prepared as Fab' or F(ab')$_2$ fragments and immobilized onto latex particles. Fab' and F(ab')$_2$ fragments are more preferable in consideration of avoiding a non-specific reaction of an antibody to Fc fragments.

An antibody used in the present invention can be obtained by first producing TAT antibodies (candidate antibodies) by a production method for monoclonal antibodies with hybridoma cells, and the like, and then selecting a first antibody and a second antibody from the TAT antibodies (candidate antibodies) according to the procedures and criteria as described above.

The combination of the first antibody and the second antibody is not particularly limited as long as it allows the assay of TAT by latex agglutination assay, but a combination of the antibodies which is minimally affected by the matrices contained in a biological sample such as plasma (background) is preferably selected.

The sensitivity required for the TAT assay reagent should be sufficient to measure the reference value with which normal subjects can be clearly distinguished from patients, or a concentration 2-fold higher than the reference value and, therefore, the reagent of the present invention is preferably a reagent capable of quantifying TAT complexes at a concentration of 10 to 15 ng/mL, more preferably a reagent capable of quantifying TAT complexes at a concentration of 3 to 4 ng/mL, and still more preferably a reagent capable of quantifying TAT complexes even at a concentration of around 1 ng/mL, in a biological sample.

The latex particles to which the above-described first and second antibodies are coupled are not particularly limited as long as they can be used in the latex agglutination reaction, but they have an average particle size of preferably 0.05 µm to 0.5 µm and more preferably 0.2 to 0.4 µm.

For the latex particles to be used, only one type of latex particle or multiple types of latex particles may be used. For example, a combination of latex particles with different particle sizes may be used. Because it is practically difficult to manufacture latex particles with a single particle size, any latex particle is specified with the average particle size of all particles. Accordingly, in the reference to an average particle size of 0.05 µm to 0.5 µm, a case comprising latex particles outside this range may also be included in the present invention. The fact that latex particles with different particle sizes are included in a given latex particle is within the common sense of those skilled in the art, and those skilled in the art will be able to establish a latex reagent by using a solution containing a group of particles having a not highly heterogeneous size distribution.

Additionally, the average particle size can be measured according to a known method and, for example, can be calculated on the basis of image analysis using a transmission electron microscope system.

The latex particle according to the present invention is not particularly limited as long as it is commonly used in the art, but examples of the latex particle include particles made from homopolymers (for example, polystyrene, methacrylate polymers, acrylate polymers, and the like) composed of polymerized vinyl monomers such as styrene, vinyl chloride, acrylonitrile, vinyl acetate, acrylate, methacrylate, and the like; particles made from butadiene copolymers (for example, styrene-butadiene copolymer, methylmethacrylate-butadiene copolymer, acrylonitrile-butadiene copolymer, and the like); and particles made from other copolymers (for example, styrene-styrenesulfonate copolymer, methacrylate copolymers, acrylate copolymers, vinyl chloride-acrylate copolymers, and the like). Examples of the latex particle include particles carrying a carboxyl group, a primary amino group, a carbamoyl group ($-CONH_2$), a hydroxyl group, an aldehyde group, or the like as a functional group and having a base body composed of any of the above-described organic particulates.

For the method to immobilize the antibodies onto latex particles, the antibodies may be immobilized according to a known method and can be immobilized by treatments commonly used in the art, such as, for example, suspending the antibody and latex particles in a buffer solution, allowing them to react at 25° C. for one hour, followed by centrifugation, blocking treatment, and the like. Moreover, a method to immobilize the antibodies onto latex particles through chemical linkage or through biotin-avidin interaction may be selected.

The coupling of the antibodies to latex particles is performed under conditions where the antibodies can maintain the above-described reactivity and specificity to TAT.

For ease of preparation of preferable reagents, an antibody-immobilized latex liquid may be prepared for every antibody as a first latex particle and a second latex particle onto which the first antibody and the second antibody have been immobilized, respectively, while the reagents may be prepared by immobilizing the first antibody and the second antibody onto a single type of latex particles. Those skilled in the art will be able to appropriately design how to immobilize the antibodies onto latex particles and to prepare reagents.

The test sample applicable to the reagent of the present invention is not particularly limited as long as it is a test sample potentially containing TAT complexes, but it is preferably a biological sample, more preferably a sample derived from any mammalian animal, and still more preferably a sample derived from human. Serum or plasma can be particularly preferably used as a sample derived from a living body. The sample is preferably a blood sample derived from a human receiving heparin (having a final concentration of, for example, 1 to 2 U/mL), and, still more preferably, can be particularly preferably used for assaying plasma derived from a human receiving heparin. The sample is preferably a sample derived from any mammalian animal and more preferably a sample derived from human.

The reagent of the present invention may be a single-reagent system or a two-reagent system. If the reagent of the present invention is a single-reagent system, TAT complexes in a biological sample can be measured by adding a suspension of latex particles carrying the immobilized first and second antibodies, respectively, and a reaction liquid containing a polycation such as hexadimethrine bromide to the biological sample, and causing an antigen-antibody reaction. If the reagent of the present invention is a two-reagent system, TAT complexes in a biological sample can be measured by adding the first reagent mainly composed of buffer ingredients and containing a polycation such as hexadimethrine bromide to the biological sample, then further adding the second reagent containing latex particles onto which the first and second antibodies have been immobilized, respectively, and causing an antigen-antibody reaction. The second reagent may also be allowed to contain the polycation and the antibody-bound latex particles. The two-reagent system is preferred for more precise measurement.

The polycation is not limited as long as it binds to heparin in a sample to inhibit binding between heparin and antithrombin. Examples of the polycation which can be used include the following.

Examples of naturally occurring polycations include: chitosans such as methyl glycol chitosan; modified dextrans such as diethylaminoethyl modified dextran; aminodextran; hydroxymethyl cellulose trimethylamine; lysozyme; spermine; spermidine; polylysine; polyarginine; polyornithine; protamine sulfate; hydroxyethyl cellulose trimethylamine; and protein.

The protein is not limited as long as it has a property of binding to heparin. A protein peptide having a sequence of BXXB, BBXB, BBBXXB, or BXXBBXB (where B represents a basic amino acid, and X represents an optional amino acid) known as a heparin-binding motif peptide can be used as the protein. Specific examples of the protein include: DNA-binding proteins such as activated factor X, heparin-binding growth factor, lactoferrin, transferrin, vitronectin, endonuclease, lipase, steroid receptor, and histone; and PF4.

Examples of synthetic polycations include polyallylamine, polyallylamine hydrochloride, poly(diallyl dialkyl amine), polyamideamine, polyamine, polyvinylbenzyltrimethylammonium chloride, hexadimethrine bromide, polydiallyldimethylammonium chloride, polyethyleneimine, polypropyleneimine, polypropylethyleneimine, polyimidazoline, polyvinylamine, polyvinyl pyridine, poly(acrylamide/methacryloxypropyltrimethylammonium bromide), poly(diaryldimethylammonium chloride/N-isopropylacrylamide), poly(dimethylaminoethyl acrylate/acrylamide), poly(dimethylaminoethyl methacrylate), polydimethylaminoepichlorohydrin, polyethyleneiminoepichlorohydrin, polymethacryloxyethyl-trimethylammonium bromide, hydroxypropylmethacryloyloxyethyl dimethyl ammonium chloride, poly(methyldiethylaminoethylmethacrylate/acrylamide), poly(methyl/guanidine), polymethylvinylpyridinium bromide, poly(vinylpyrrolidone-dimethylaminoethyl methacrylate), and polyvinylmethylpyridinium bromide.

Examples of these polycations include hexadimethrine bromide, polyalkylene amines such as polyethyleneimine and polypropylethyleneimine, protamine sulfate, polylysine, polyornithine, and aminodextran. Hexadimethrine bromide or protamine sulfate is particularly preferably used.

The known molecular weight of the polycation is a mass average molecular weight of several hundreds to several millions. A polycation having a molecular weight of 1,000 to 100,000 can be preferably used in the present invention, and a polycation having a molecular weight of 1,000 to 10,000 can be more preferably used.

The polycation having a final concentration of 0.0002 to 1% (w/v) is preferably allowed to exist in a reaction system, the polycation having a final concentration of 0.0005 to 0.1% (w/v) is more preferably allowed to exist in the reaction system, and the polycation having a final concentration of 0.001 to 0.05% (w/v) is still more preferably allowed to exist in the reaction system.

A negative charge such as $SO^{3-}$, $SO^{4-}$, or $COO^-$ typically exists on latex particles. Therefore, addition of a polycation into a reagent can be easily considered to cause agglutination due to a positive charge of a polycation even in the absence of a substance to be measured, and there is a concern that the addition affects a measurement system. Therefore, hesitation in using such a polycation usually occurs. However, the present inventor found that an antithrombin multimer generated by binding of heparin to antithrombin in a sample is dissociated by a polycation such as hexadimethrine bromide. Use of the above-described polycation surprisingly enables only the effect of heparin to be circumvented without causing such a side effect (agglutination) and TAT complexes to be precisely assayed.

The degree of agglutination of latex particles can be measured, for example, using absorbance, while the concentration of TAT complexes in a sample can be quantified by searching for a concentration corresponding to the degree of agglutination on a previously obtained standard curve of the reference. Additionally, the measurement of absorbance may be performed at a measurement wavelength of normally 340 nm to 1000 nm and preferably 500 nm to 900 nm. When the latex agglutination reaction is analyzed by photometry, the kinetics of agglutination or the variation in agglutination over a fixed time interval during the proceeding of the latex agglutination reaction can be determined by photometry. For example, when the measurement of absorbance is performed, the kinetics of absorbance changes or the variation in absorbance over a fixed time interval within the period from 30 seconds to 5 minutes after the start of the latex agglutination reaction can be determined by photometry. The reaction temperature is preferably from 10 to 50° C. and more preferably from 20 to 40° C. The reaction time can be appropriately determined, and the measurement may be performed, for example, within a reaction time of 10 to 15 minutes on a general-purpose auto-analyzer. Additionally, those skilled in the art will be able to appropriately determine the reaction temperature, the reaction time, the measurement wavelength, the measurement time, the reagent composition, the latex concentration, the concentration of an antibody to be immobilized onto latex particles, and the concentrations of various additive agents in analysis using an optical instrument or a general-purpose auto-analyzer.

The concentration of latex particles used in the present invention is not particularly limited as long as it is a concentration applicable to a reagent for an immunological assay based on latex agglutination assay, but the concentration of latex particles during the reaction required for the TAT assay is preferably 0.005% (w/v) to 0.2% (w/v) and more preferably 0.01% (w/v) to 0.1% (w/v).

The reagent of the present invention may further comprise, in addition to the latex particles onto which the antibodies have been immobilized, excipients which can be added to a reagent for an immunological assay based on latex agglutination assay, such as, for example, a buffer, an agglutination promoter, a nonspecific-reaction suppressant, a sensitizing agent, and the like. Examples of the sensitizing agent which can be added to the reagent of the present invention include sodium alginate, propylene glycol alginate, and the like. Moreover, a water soluble polymer or protein is preferably used as an agglutination promoter which can be added to the reagent of the present invention. Examples of the agglutination promoter include water soluble polymers such as dextran and dextran sulfate, polyvinyl alcohol, polyethylene glycol, polyvinylpyrrolidone, and the like; albumins such as bovine serum albumin; and globulins such as γ-globulin.

As the buffer, for example, a buffer having a buffer capacity at a pH of 5.8 to 6.6 can be used. The pH is more preferably 6.0 to 6.4, still more preferably 6.1 to 6.3, and particularly preferably 6.15 to 6.25. In the case of a single-reagent system the pH of the reagent should be adjusted into the above-described range, while in the case of a two-reagent system the reagents should be composed such that the pH is in the above-described range when they are mixed. For example, in an aspect where the reagent system comprises a first reagent mainly composed of buffer ingredients and a second reagent containing latex particles onto which the antibodies have been immobilized, the pH of the first reagent is adjusted into the above-described range, and the pH of the mixture is in the above-described range when both the reagents are mixed.

The pH may be regulated by a pH regulator and is preferably adjusted by a buffer solution. A buffer solution such as Tris buffer. Bis-Tris buffer, phosphate buffer, or Good's buffer is preferably used and the concentration of the buffer solution during the reaction is preferably 10 to 500 mmol/L and more preferably 20 to 200 mmol/L.

Examples of the nonspecific-reaction suppressant which can be added to the reagent of the present invention include antibodies or receptors against substances responsible for a nonspecific reaction; buffer solutions, such as Tris buffer, phosphate buffer, glycine buffer, borate buffer, citrate buffer, acetate buffer, or Good's buffer; chelating agents, such as EDTA, CyDTA, DTPA, EGTA, NTA, and NTP; salts, such as sodium chloride, potassium chloride, sodium sulfate, calcium sulfate, magnesium sulfate, calcium carbonate, and sodium carbonate; and non-ionic surfactants, such as fatty acid diethanolamides, polyoxyethylene alkyl ethers, polyoxyethylene alkylphenyl ethers, fatty acid sorbitan esters, alkyl polygulcosides, alkyl monoglyceryl ethers, polyoxyethylene sorbitan fatty acid esters, fatty acid alkanolamides, and alkyl glycosides.

The reagent of the present invention may include TAT complexes which can be used as a standard substance. The TAT complexes may be TAT complexes purified from a living body or synthesized by recombinant DNA technology and the like. The synthetic TAT complexes can be obtained, for example, by incubating in vitro thrombin and antithrombin molecules available as biologics. Moreover, TAT complexes can also be synthesized by recovering and purifying and mixing the components which have been expressed using a known translation system in E. coli, mammalian cells, insect cells infected with baculovirus, and the like.

EXAMPLES

Example 1: Preparation of Synthetic TAT Complexes

A commercially available human thrombin formulation (manufactured by Japan Blood Products Organization) and a commercially available antithrombin formulation (manufactured by Japan Blood Products Organization) were separately diluted with PBS (produced by dissolving Dulbecco's PBS (−) powder "Nissui (manufactured by Nissui Pharmaceutical Co., Ltd.)" to a concentration of 9.6 g/L) and those dilutions were mixed at a molar ratio of 1:3 and then allowed to react at 37° C. for 30 minutes. After the 30 minutes, DFP (diisopropyl fluorophosphate, manufactured by Wako Pure Chemical Industries, Ltd.) was added to a concentration of 0.75 mM to stop the reaction.

Because unreacted thrombin and antithrombin were contained in the obtained reactant, purification was performed with a Hiload 26/60 Superdex 200 HR (manufactured by GE Healthcare) previously equilibrated with 50 mM Tris-HCl buffer (pH 7.4) containing 500 mM NaCl.

TAT fractions were recovered after identification by SDS-PAGE. The obtained TAT fraction was diluted with saline containing 0.5% BSA and analyzed using a CLEIA reagent (STACIA (registered trademark) CLEIA TAT, manufactured by LSI Medience Co.) to determine the concentration. The thus-obtained TAT complexes were used as synthetic TAT complexes.

Example 2: Preparation of Anti-TAT Antibody

A cell fusion method was carried out according to the method described in Tamie Ando and Tatsuo Iwasaki, "Monoclonal Antibody/Hybridoma and ELISA" (Kodansha Ltd.).

The synthetic TAT complex prepared in Example 1 in an amount of 50 μg was mixed with Freund's complete adjuvant (manufactured by DIFCO) to provide an administered antigen.

The antigen was administered to BALB/c mice (female, four weeks old) three times at an interval of two weeks and 25 μg of the antigen, that is, half the amount of the original administered antigen was injected intravenously at the fourth administration.

One week later, lymphocytes were isolated from the spleen and mixed with P3x63-Ag.8 myeloma cells and then fused using polyethylene glycol (PEG 4000, manufactured by Merck).

Hybridoma cells were selected in HAT selection medium and then screened one week later for hybridoma clones producing an antibody of interest on the basis of the binding activity for the synthetic TAT complex. That is, the synthetic TAT complex was individually diluted with 0.05 M carbonate buffer (pH 9.5) to a concentration of 0.2 μg/mL and added at 50 μL/well to an immuno plate (Maxisorp, manufactured by NUNC). After the reaction at 4° C. overnight, each well was washed three times with PBS containing 0.05% Tween-20 and then blocked by adding thereto 100 μL of PBS containing 1.0% BSA. Subsequently, the culture supernatant was added in a volume of 50 μL to each well and allowed to react at 37° C. for one hour and then each well was washed three times with PBS containing 0.05% Tween-20. A peroxidase-labeled anti-mouse immunoglobulin antibody (manufactured by Dako) was diluted 1000 times in PBS containing 0.05% Tween-20 and then added in a volume of 50 μL to each well.

After the reaction at 37° C. for one hour, each well was washed five times in a similar way and then a solution of o-phenylenediamine (manufactured by Wako Pure Chemical Industries, Ltd.) was added in a volume of 50 μL to each well. After the reaction at room temperature for 5 to 10 minutes, the reaction was stopped with 2 N sulfuric acid.

The absorbance was measured at 492 nm on a plate spectrophotometer (EL312e, manufactured by BioTek Instruments, Inc.). Cells producing antibodies showing good reactivity to the synthetic TAT complex were selected and then cloned by limiting dilution. Ten days later, those cells were further screened to obtain hybridoma clones producing antibodies which react with the synthetic TAT complex.

Example 3: Preparation of Anti-Thrombin Antibody

Anti-thrombin antibodies were obtained by a method similar to that in Example 2 using thrombin as an immunizing antigen. Antibodies specifically reacting with thrombin were selected and one of those clones was used as an anti-thrombin antibody (T-1).

Example 4: Evaluation of Antibody Specificity by Indirect Inhibition ELISA

Figure 2:
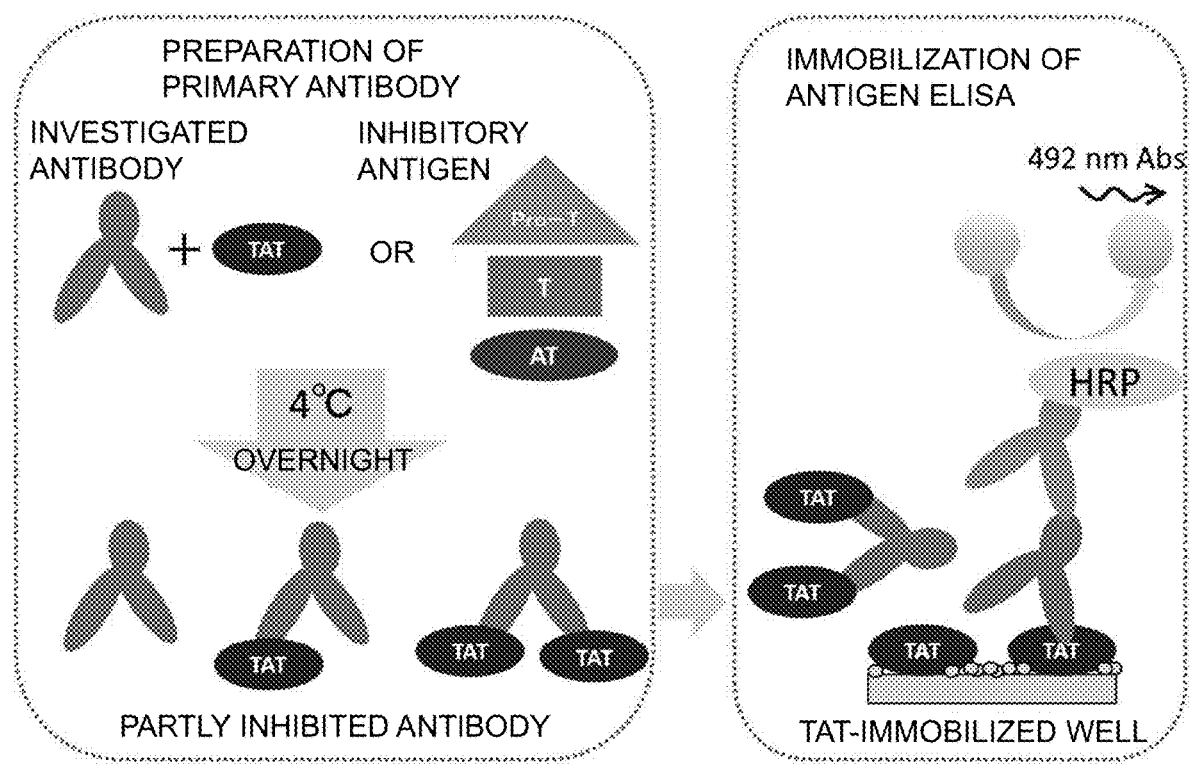
FIG. 2 is a schematic view of a reaction system based on indirect inhibition ELISA assay.

The reactivity of each antibody was evaluated by indirect inhibition ELISA. A schematic model of the reaction system by indirect inhibition ELISA is illustrated in FIG. 2.

Every TAT-recognizing antibody (anti-TAT antibody) candidate to be evaluated at a concentration of 0.04 to 0.4 μg/mL was mixed and incubated with each inhibitory antigen (prothrombin (manufactured by Enzyme Research Laboratories), thrombin, antithrombin, synthetic TAT complex). Those candidate antibodies, including a group of inhibited antibodies, were used as primary antibodies and allowed to bind to synthetic TAT complexes immobilized onto 96-well plates. Furthermore, a peroxidase-labeled anti-mouse immunoglobulin antibody (manufactured by Dako) was used as a secondary antibody and allowed to bind to the plates and then a chromogenic substrate was added to the plates to measure the absorbance. Moreover, the percentage of residual antibody in each candidate antibody was calculated based on the rate of color change.

For a particular antibody (TAT-5), the values of absorbance obtained when each inhibitory antigen was used are set forth in Table 1, while the ratios of residual antibody calculated from the values of absorbance are set forth in Table 2.

For example, if the concentration of the TAT inhibitory antigen is 10 µg/mL, the percentage of residual antibody will be 285/1066×100=26.7(%). The percentage of residual antibody in each antibody was calculated for each concentration of each antigen. Additionally, in the tables, Pro-T represents prothrombin, T represents thrombin, and AT represents antithrombin.

TABLE 1

Results from Measurement on Indirect Inhibition ELISA

| Inhibitory antigen | Pro-T | T | AT | TAT |
|---|---|---|---|---|
| 0 | 1066 | 1066 | 1066 | 1066 |
| 0.016 | 1074 | 1059 | 1059 | 1063 |
| 0.08 | 1062 | 1062 | 1059 | 1045 |
| 0.4 | 1085 | 1067 | 1065 | 965 |
| 2 | 1064 | 1049 | 1033 | 661 |
| 10 | 1071 | 1057 | 1001 | 285 |
| 50 | 1072 | 1056 | 789 | 112 |

(Concentration of inhibitory antigen: µg/mL, absorbance (492 nm × 1000), each measurement for N = 2 (average value))

TABLE 2

Percentage (%) of Residual Antibody

| Inhibitory antigen | Pro-T | T | AT | TAT |
|---|---|---|---|---|
| 0 | 100.0% | 100.0% | 100.0% | 100.0% |
| 0.016 | 100.8% | 99.3% | 99.3% | 99.7% |
| 0.08 | 99.6% | 99.6% | 99.3% | 98.1% |
| 0.4 | 101.8% | 100.1% | 99.9% | 90.5% |
| 2 | 99.8% | 98.4% | 96.9% | 62.0% |
| 10 | 100.5% | 99.2% | 93.9% | 26.7% |
| 50 | 100.6% | 99.1% | 74.0% | 10.5% |

(Concentration of inhibitory antigen: µg/mL)

Moreover, the amount of the TAT antigen required to achieve an inhibition rate corresponding to the percentage of residual antibody obtained by inhibition with antithrombin at 50 µg/mL was calculated and compared with the amount of antithrombin to obtain the difference (fold increase) in the reactivity of each antibody to TAT relative to that to antithrombin. A larger difference in the reactivity of an antibody indicates the higher specificity of the antibody to TAT relative to that to antithrombin. Calculation was performed based on the TAT-inhibition curve (the logarithm of the concentration of the added inhibitory antigen versus the percentage of residual antibody) drawn with the spline function.

Figure 3:
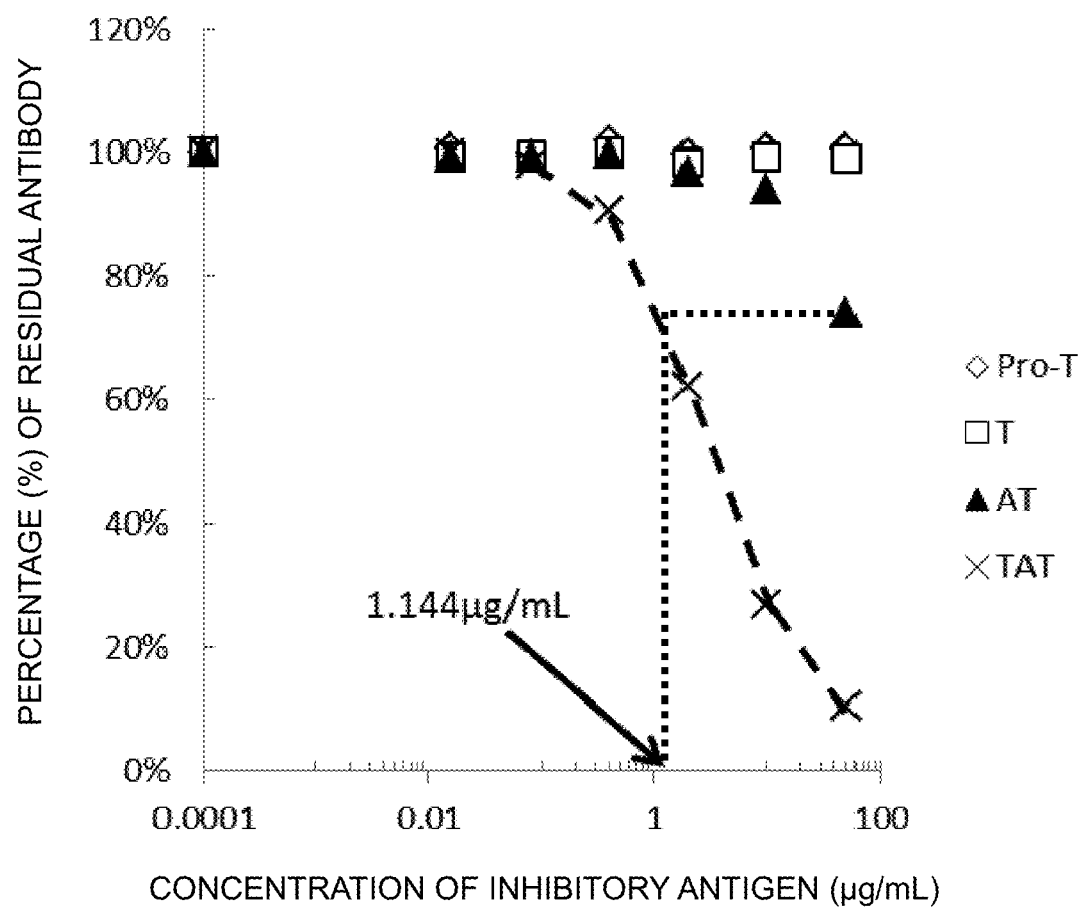
FIG. 3 is a view illustrating results from the evaluation of the binding of clone TAT-5 to each antigen by indirect inhibition ELISA assay.

For example, in the case of TAT-5, the percentage of residual antibody obtained with antithrombin at 50 µg/mL is 74.0%, while the amount of the TAT antigen required to achieve a percentage of residual antibody similar to that percentage is 1.144 µg/mL. That is, the difference in reactivity proves to be 50/1.144=44-fold (FIG. 3).

Furthermore, the above-described fold increase was calculated for 27 antibody clones. The difference (fold increase) in the amount of the added TAT complexes relative to that of the added antithrombin was 100 or more in thirteen among them, 1000 or more in seven among them, and 10000 or more in two among them. Five among those antibodies are presented in Table 3.

TABLE 3

| Clone | Concentration during reaction (µg/mL) | Inhibition 50 µg/mL AT (percentage (%) of residual antibody) | TAT required to achieve inhibition corresponding to case 50 µg/mL AT (µg/ml) | Fold increase (fold) |
|---|---|---|---|---|
| TAT-1 | 0.04 | 88.2 | 0.001 | 49892 |
| TAT-2 | 0.08 | 92.3 | 0.029 | 1700 |
| TAT-3 | 0.08 | 89.4 | 0.230 | 218 |
| TAT-4 | 0.08 | 18.0 | 0.720 | 69 |
| TAT-5 | 0.40 | 74.0 | 1.144 | 44 |

Example 5: Effect of Hexadimethrine Bromide in Heparin-Added Plasma (Model Sample)

First reagent: For a first reagent, 100 mM Bis-Tris (manufactured by DOJINDO LABORATORIES, pH 6.2), 700 mM NaCl (manufactured by Wako Pure Chemical Industries, Ltd.), 0.05% EMULGEN 150 (manufactured by Kao Corporation), 0.20% sodium alginate (manufactured by Wako Pure Chemical Industries, Ltd.), 0.15% BSA (manufactured by Sigma-Aldrich), and 0.05% hexadimethrine bromide (manufactured by Sigma-Aldrich) were used. Moreover, for a Comparative Example, a reagent obtained by removing hexadimethrine bromide from the first reagent was used.

Second reagent: A reagent (second reagent A: latex particle concentration of 0.01%) was obtained by diluting and mixing, with 0.05% sodium azide solution, polystyrene latex particles which adsorbed a mouse monoclonal antibody TAT-1 having a level of reactivity to TAT that is 100 or more times higher than the reactivity to antithrombin and reacting with the antithrombin part of a TAT complex and polystyrene latex particles which adsorbed an antithrombin mouse monoclonal antibody so that the particles sensitized with each antibody had an absorbance of 1.0 at 700 nm. A reagent (second reagent B) was obtained by diluting and mixing, with 0.05% sodium azide solution, only polystyrene latex particles which adsorbed a mouse monoclonal antibody having a level of reactivity to TAT that is 100 or more times higher than the reactivity to antithrombin and reacting with the antithrombin part of a TAT complex so that the particles had an absorbance of 1.0 at 700 nm. Each reagent was used as a second reagent.

Sample: Either normal human pooled plasma to which a heparin sodium injection "Tanabe" (manufactured by Mitsubishi Tanabe Pharma Corporation) was added so that it was 1 or 2 U/mL or normal human pooled plasma to which heparin was not added was measured.

Measurement Instrument: 7170S (Manufactured by Hitachi High-Technologies Corporation)

Parameters: Parameters were set to 12 µL of sample volume, 90 µL of the first reagent, 90 µL of the second reagent, 570 nm of main wavelength, and 800 nm of subsidiary wavelength. A value obtained by subtracting the absorbance at the 20th photometric measurement point from the absorbance at the 34th photometric measurement point was regarded as ΔAbs, and the measurement was performed.

Results and Discussion

Figure 4:
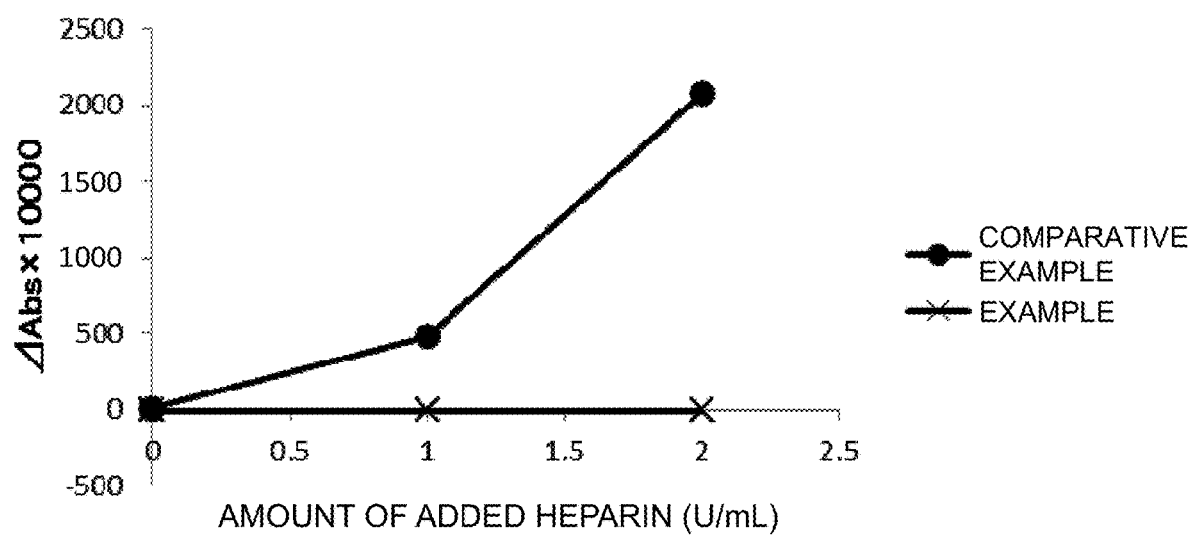
FIG. 4 is a view illustrating the effect of hexadimethrine bromide in heparin-added plasma (model sample).
Figure 4:
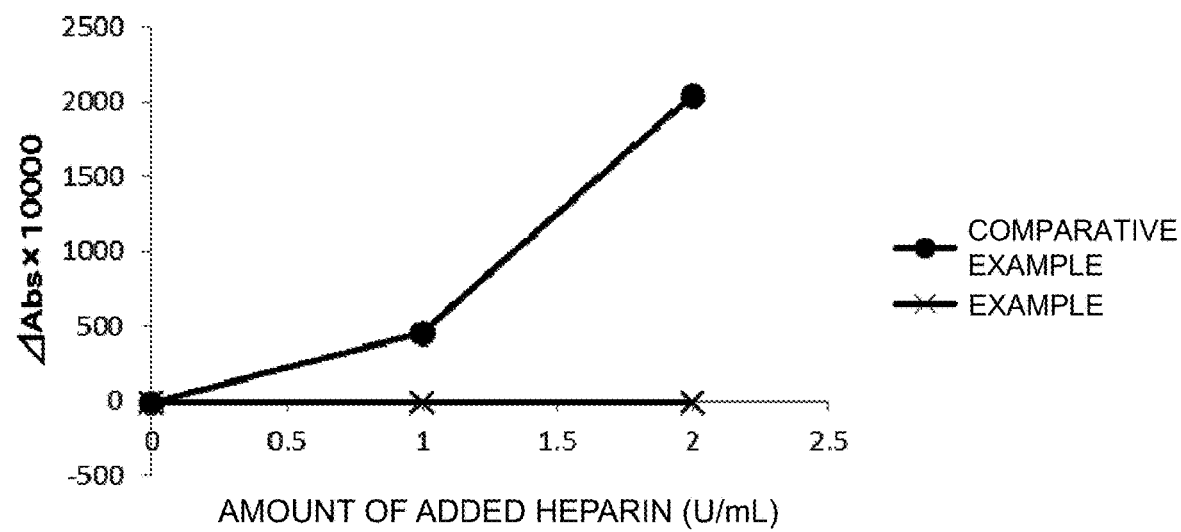

The results are illustrated in FIG. 4. Concentration-dependent nonspecific agglutination of heparin was observed at similar levels in both the second reagents A and B in the case of using the first reagent of the Comparative Example (without hexadimethrine bromide) while the agglutination was observed in neither the second reagent A nor B in the case of using the first reagent of Examples (with hexadimethrine bromide). This suggested that the nonspecific agglutination of heparin-antithrombin complexes is caused by particles adsorbing an antibody recognizing the antithrombin part of a TAT complex, and the addition of hexadimethrine bromide allows the heparin-antithrombin complexes to disappear.

Example 6: Examination of Amount of Added Hexadimethrine Bromide

First reagent: The same first reagent as that in Example 5 was used except that the amount of added hexadimethrine bromide was changed in a range between 0 and 0.05% (w/v).

Second reagent: The second reagent A in Example 5 was used.

Sample: Normal human pooled plasma to which 2 U/mL of a heparin sodium injection "Tanabe" was added or normal human pooled plasma to which 2 U/mL of a heparin sodium injection "Tanabe" was added and serum was added to have a TAT concentration of 50 ng/mL Measurement instrument and parameters: The same measurement instrument and parameters as those in Example 5 were used to perform measurement.

Figure 5:
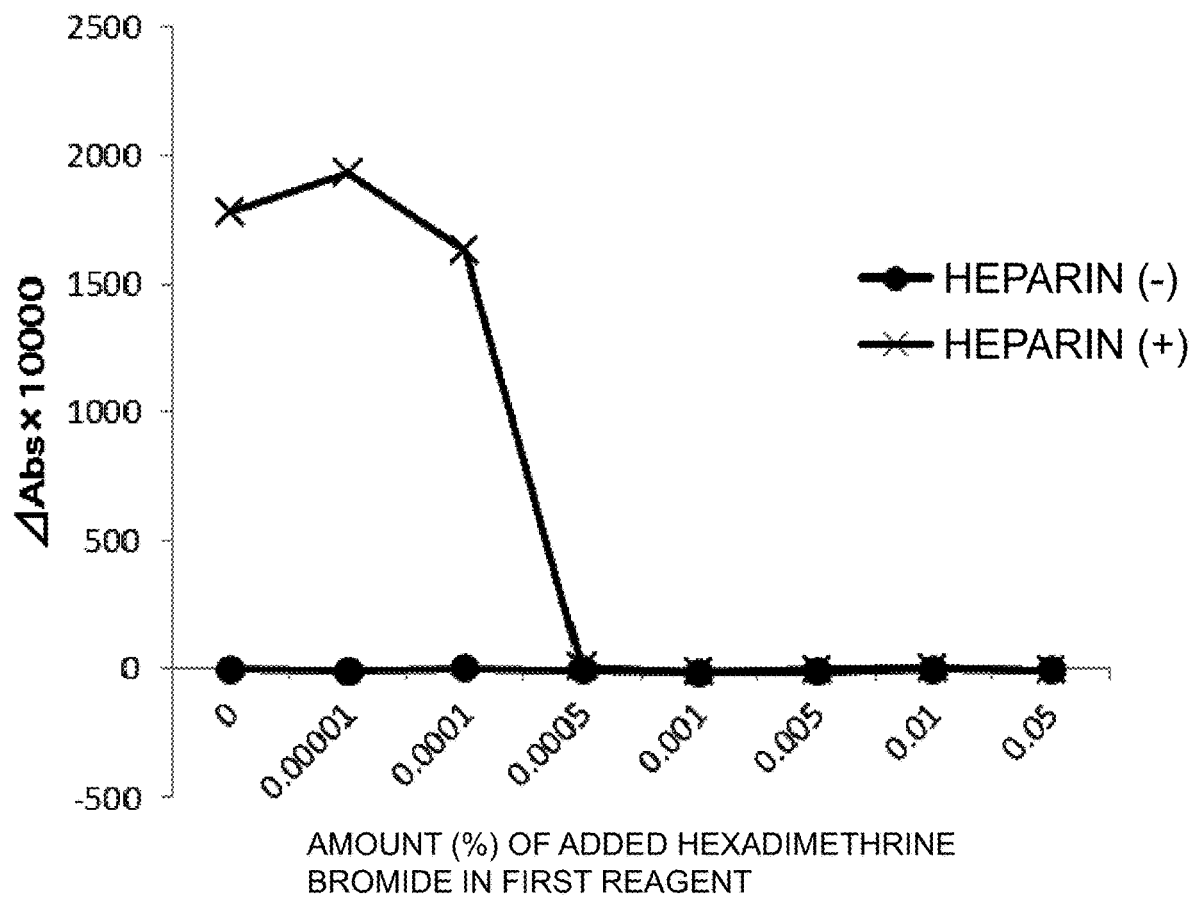
FIG. 5 is a view illustrating detection results from each of heparin-treated blood and heparin-untreated blood in the case of changing the concentration of hexadimethrine bromide.
Figure 6:
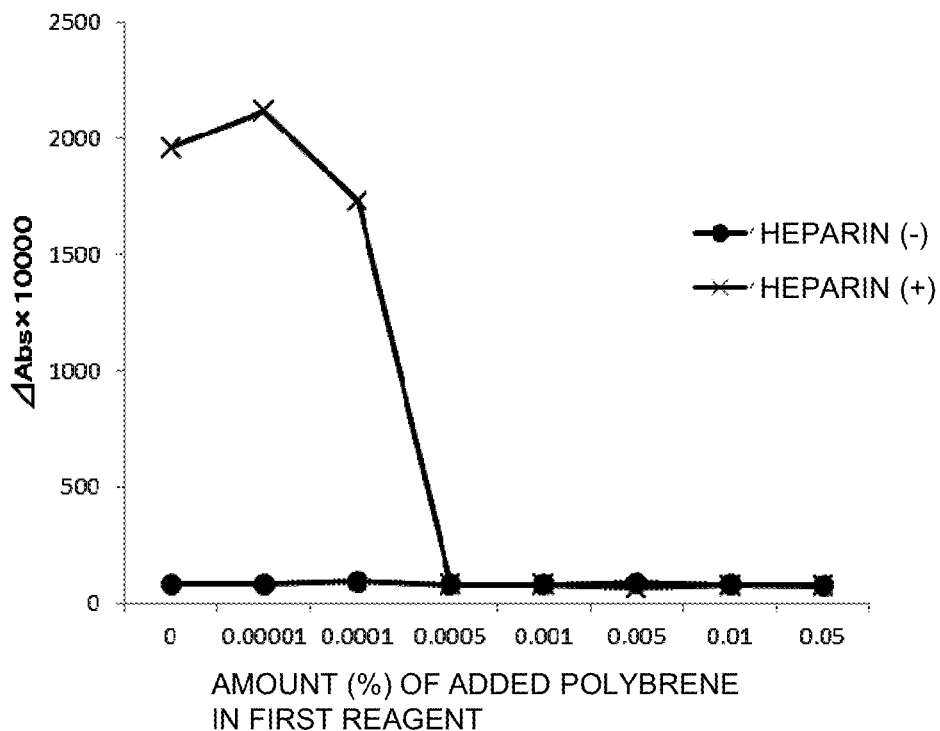
FIGS. 6A and 6B are views illustrating detection results in the case of further adding serum to heparin-treated blood or heparin-untreated blood so that the concentration of TAT complexes is 50 ng/mL and changing the concentration of hexadimethrine bromide (polybrene) in each blood. The lower diagram (FIG. 6B) is an enlarged diagram of the upper diagram (FIG. 6A).
Figure 6:
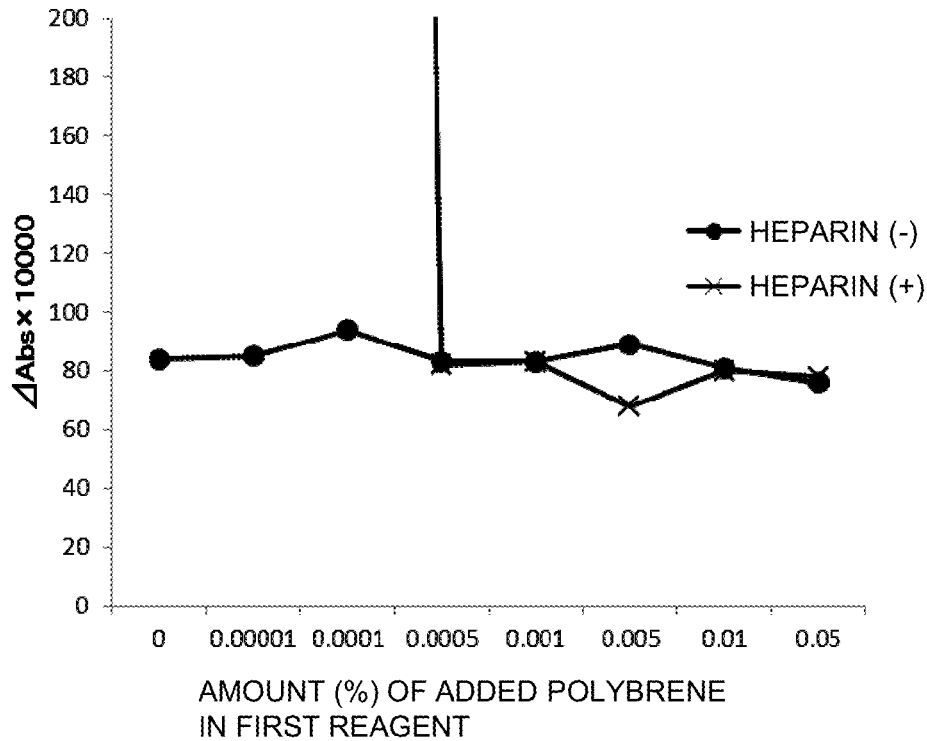

Results and discussion: The results are illustrated in FIG. 5, FIGS. 6A and 6B. The addition of 0.0005% (final concentration of 0.0002%) hexadimethrine bromide (polybrene) to 2 U/mL of heparin exhibited an effect. Moreover, it was confirmed that nonspecific agglutination of latex particles due to positive charge of hexadimethrine bromide did not occur in base plasma to which heparin was not added, until addition of 0.05% (final concentration % of 0.023%). Accordingly, it was found that hexadimethrine bromide is preferably equal to or more than 0.0005% (final concentration of 0.0002%), and more preferably equal to or more than 0.005% (final concentration of 0.002%).

As illustrated in FIG. 6A, it was confirmed that even the addition of a polycation did not greatly influence a reaction of detection of TAT complexes of interest. FIG. 6B is an enlarged diagram of the vicinity of the baseline.

Example 7: Effect of Protamine Sulfate

First reagent: A first reagent was prepared in the same manner as that in Example 5 except that the amount of added protamine sulfate (manufactured by Wako Pure Chemical Industries, Ltd.) instead of hexadimethrine bromide was changed in a range between 0 and 0.01% (w/v).

Second reagent: The second reagent A of Example 5 was used.

Sample: Normal human pooled plasma to which 2 U/mL of a heparin sodium injection "Tanabe" was added; Measurement instrument and parameters: The same measurement instrument and parameters as those in Example 5 were used to perform measurement.

Results and Discussion

Figure 7:
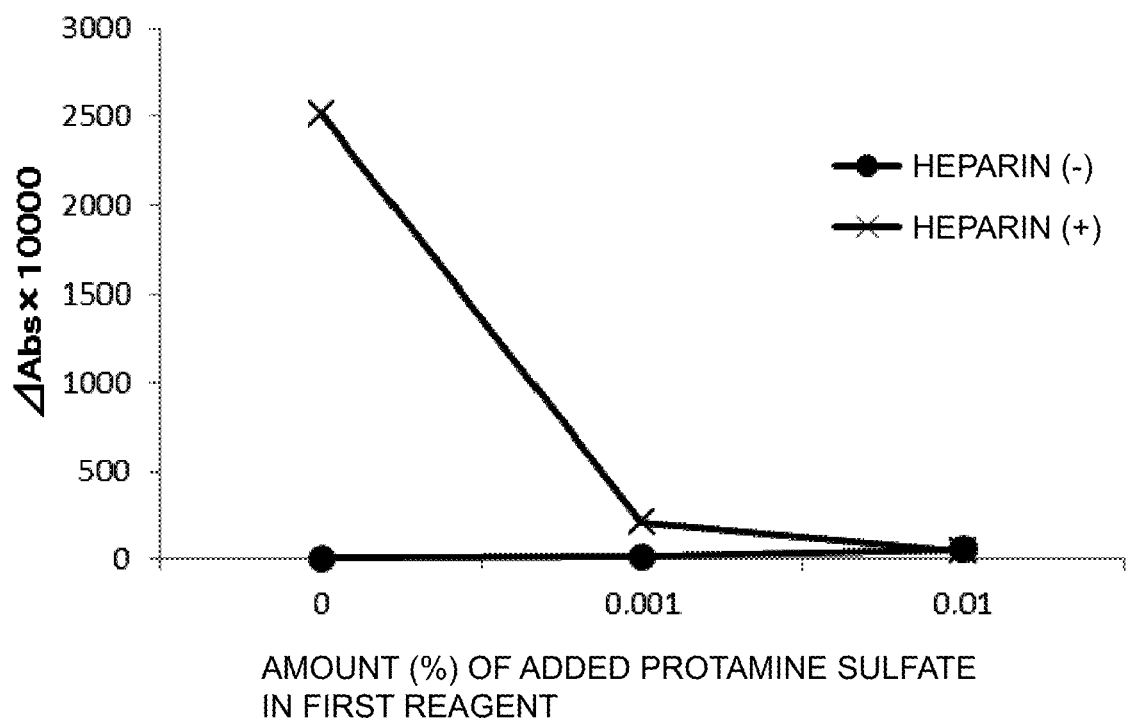
FIG. 7 is a view illustrating detection results in the case of changing the concentration of protamine sulfate in each of heparin-treated blood and heparin-untreated blood. The lower diagram is an enlarged diagram of the upper diagram.
Figure 7:
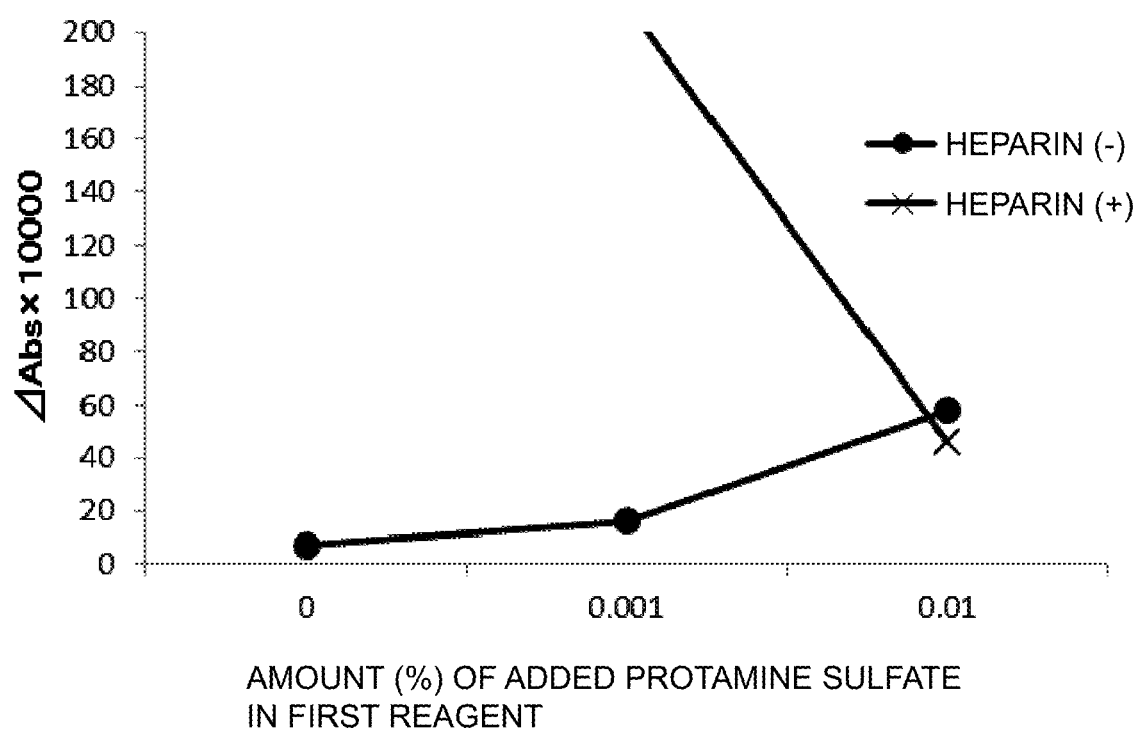

The results are illustrated in FIG. 7. In the case of adding 0.001% (final concentration of 0.0005%) or more of protamine sulfate, the absorbance of heparin-added plasma greatly decreased, and improvement was seen in comparison with the case of adding no protamine sulfate. Furthermore, in the case of adding 0.01% (final concentration of 0.005%) of protamine sulfate, nonspecific agglutination due to the addition of heparin was confirmed to be approximately suppressed similarly in the case of adding hexadimethrine bromide. Accordingly, it was found that protamine sulfate is preferably equal to or more than 0.001% (final concentration of 0.0005%), and more preferably equal to or more than 0.01% (final concentration of 0.005%).

Example 8: Effect of Hexadimethrine Bromide in Actual Samples

First reagent: The same first reagent as that in Example 5.

Second reagent: The second reagents A and B of Example 5 were used.

Samples: Since nonspecific reaction was observed, two samples of Na-citrate plasma (samples 1 and 2) to which heparin preparation was estimated to be administered were used.

Measurement instrument and parameters: The same measurement instrument and parameters as those in Example 5 were used to perform measurement.

Results and Discussion

Figure 8:
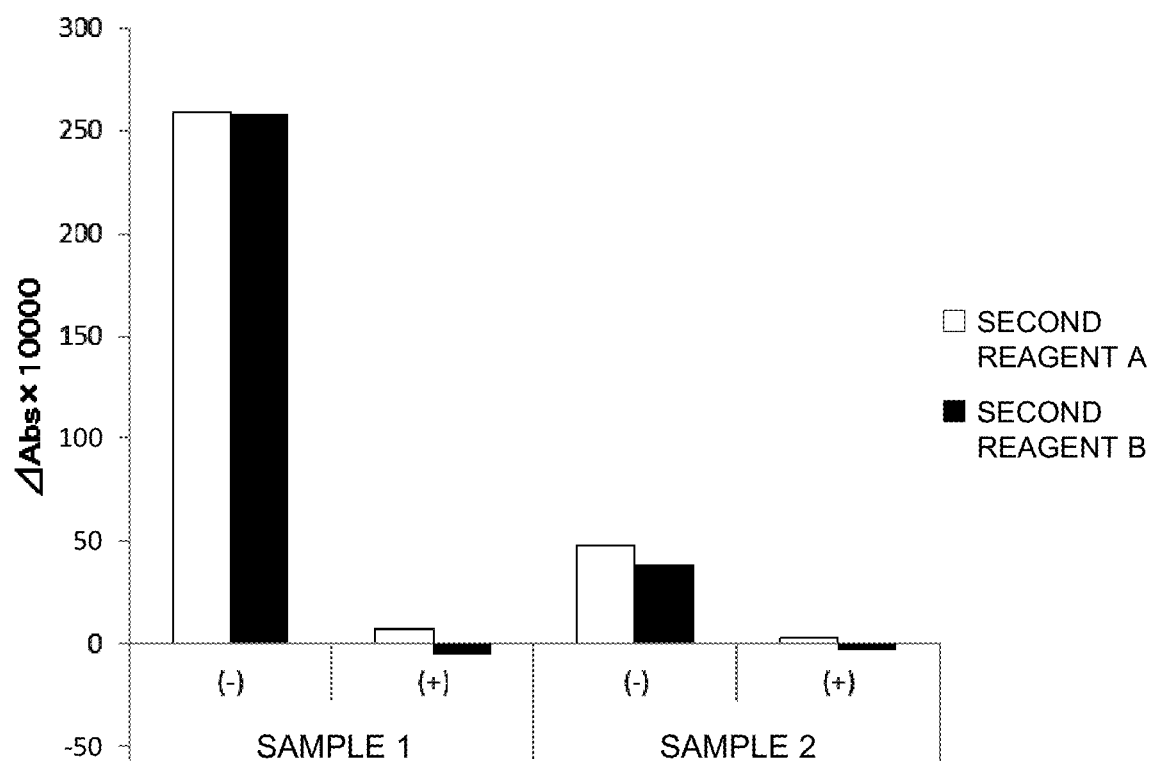
FIG. 8 is a view illustrating the assay results of the evaluation of a clinical sample using a second reagent A or a second reagent B in the presence (+) or absence (−) of hexadimethrine bromide.

The results are illustrated in FIG. 8. When hexadimethrine bromide was not added, a high signal was detected even in the case of using each of the second reagent A and the second reagent B. In contrast, the addition of hexadimethrine bromide allowed nonspecific agglutination to disappear and enabled TAT-specific detection in the case of using the second reagent A, that is, two kinds of antibodies. Based on the above, the effect of hexadimethrine bromide was also confirmed in the actual plasma samples.

As described above, the dissociation of an antithrombin multimer, generated by binding of heparin to antithrombin in a sample, by a polycation such as hexadimethrine bromide is a surprising effect found by the present inventor. Use of a polycation enabled only the effect due to heparin to be circumvented and TAT complexes to be precisely assayed, without causing such a side effect.

What is claimed is:

1. A method for assaying a TAT complex existing in a blood plasma sample from a patient receiving heparin, said blood sample comprising antithrombin multimers resulting from formation of heparin/antithrombin complexes the method comprising:
    assaying a TAT complex in the blood plasma sample from the patient by performing a latex agglutination assay comprising contacting the sample with a latex agglutination assay reagent mixture,
    wherein said reagent mixture comprises: (i) a first anti-TAT antibody which recognizes a TAT complex by binding to an antithrombin part of the TAT complex bound to latex, said first anti-TAT antibody has a reactivity to the TAT complex that is 100 times or higher-than a reactivity to free antithrombin; (ii) a second anti-TAT antibody which recognizes a TAT complex by binding to a thrombin part of the TAT complex bound to latex; and (iii) a polycation selected from the group consisting of hexadimethrine bromide and protamine sulfate,
    wherein the final concentration of hexadimethrine bromide in the assay is 0.0002 to 0.002% (w/v), wherein the final concentration of protamine sulfate in the assay is 0.0005% to 0.005% (w/v), wherein the antithrombin multimers are capable to agglutinate in the presence of the first anti-TAT antibody of (i) and second anti-TAT antibody of (ii) bound to latex, thereby causing non-specific agglutination; and wherein the polycation dissociates the antithrombin multimers, thereby reducing nonspecific agglutination.

2. The method according to claim 1, wherein the polycation is hexadimethrine bromide.

3. The method according to claim 1, wherein the polycation is protamine sulfate.

\* \* \* \* \*